(12) United States Patent
Kadoch

(10) Patent No.: US 7,338,489 B2
(45) Date of Patent: Mar. 4, 2008

(54) CUTTING TOOL FOR TISSUE SURGICAL RESECTION

(76) Inventor: Isaac-Jacques Kadoch, 19, avenue Ferdinand Buisson, 75016 Paris (FR)

(*) Notice: Subject to any disclaimer, the term of this patent is extended or adjusted under 35 U.S.C. 154(b) by 569 days.

(21) Appl. No.: 10/311,249

(22) PCT Filed: Jun. 15, 2001

(86) PCT No.: PCT/FR01/01886

§ 371 (c)(1),
(2), (4) Date: Jun. 6, 2003

(87) PCT Pub. No.: WO01/95814

PCT Pub. Date: Dec. 20, 2001

(65) Prior Publication Data

US 2004/0092986 A1    May 13, 2004

(30) Foreign Application Priority Data

Jun. 15, 2000   (FR) .................................. 00 07643

(51) Int. Cl.
*A61B 18/18* (2006.01)
(52) U.S. Cl. ........................................................ 606/45
(58) Field of Classification Search ................ 606/167, 606/27–52
See application file for complete search history.

(56) References Cited

U.S. PATENT DOCUMENTS

| 2,419,114 | A |   | 4/1947  | Briegel           |        |
|-----------|---|---|---------|-------------------|--------|
| 2,730,102 | A |   | 1/1956  | Hood              |        |
| 5,196,011 | A |   | 3/1993  | Korth et al.      |        |
| 5,324,288 | A |   | 6/1994  | Billings et al.   |        |
| 5,902,300 | A | * | 5/1999  | Hahnen et al.     | 606/46 |
| 5,919,191 | A | * | 7/1999  | Lennox et al.     | 606/48 |
| 6,494,881 | B1| * | 12/2002 | Bales et al.      | 606/45 |

FOREIGN PATENT DOCUMENTS

GB    2 261 170    5/1993

* cited by examiner

*Primary Examiner*—Roy D. Gibson
*Assistant Examiner*—Pete Vrettakos
(74) *Attorney, Agent, or Firm*—Young & Thompson

(57) ABSTRACT

A cutting tool for tissue surgical resection instruments, such as electric or ultrasonic bistoury, includes a connector element (5) supported in its upstream portion by the bistoury, a thin cutting element (7) integral with the connector element (5), and forming a plane, and a guide element (15) spaced apart from the cutting element (7) by a distance (b) equal to the thickness of the tissue elements to be removed and designed, during the cutting procedure, to be urged in contact with the surface (1) thereof. The guide element (15) is located in the cutting element plane, and its surface (1) adapted to be urged in contact with the tissues is larger than the corresponding surface of the cutting element (7).

12 Claims, 2 Drawing Sheets

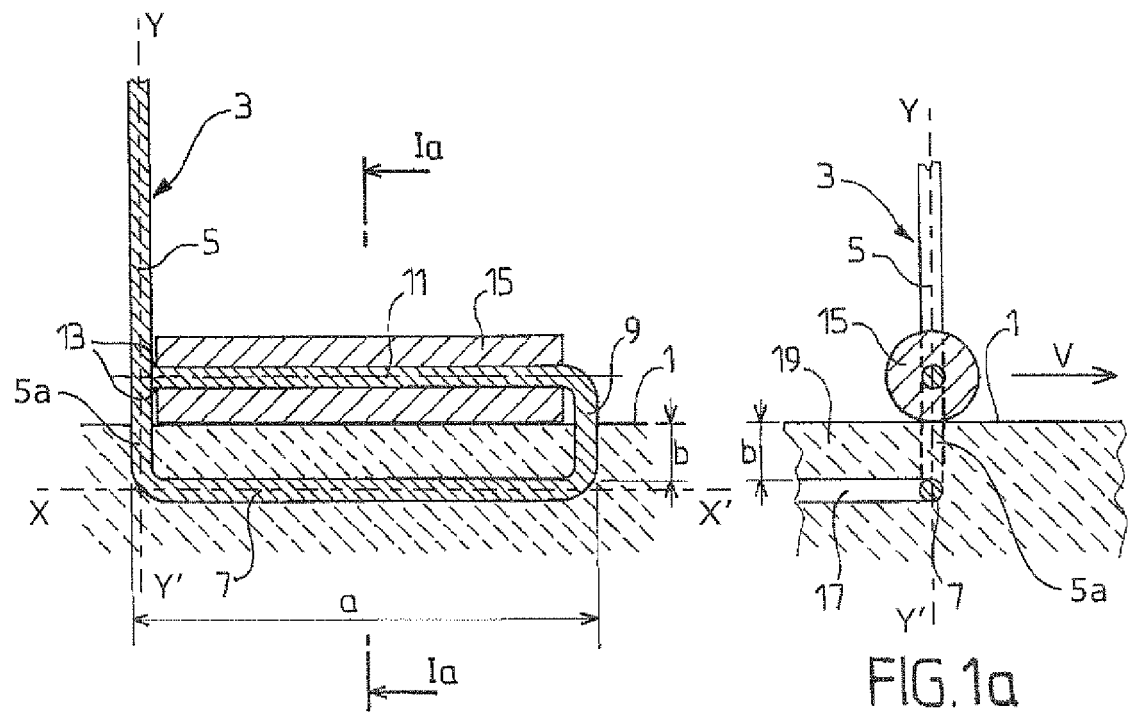
FIG. 1
FIG. 1a
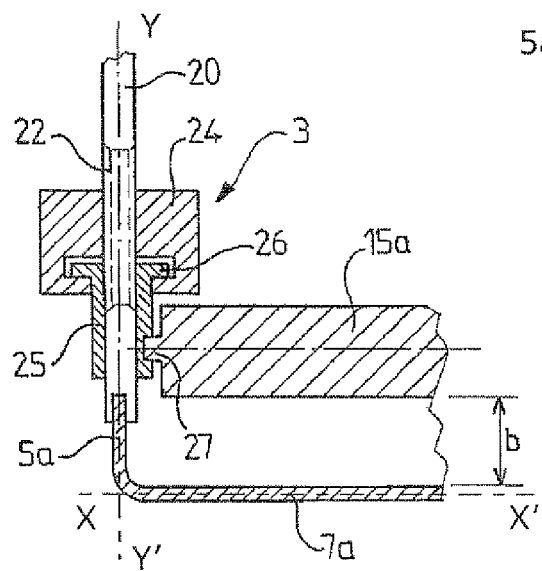
FIG. 2
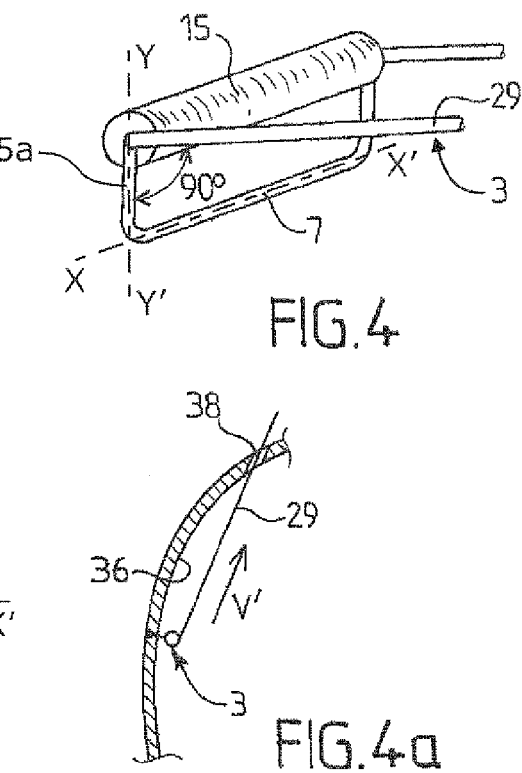
FIG. 4
FIG. 4a

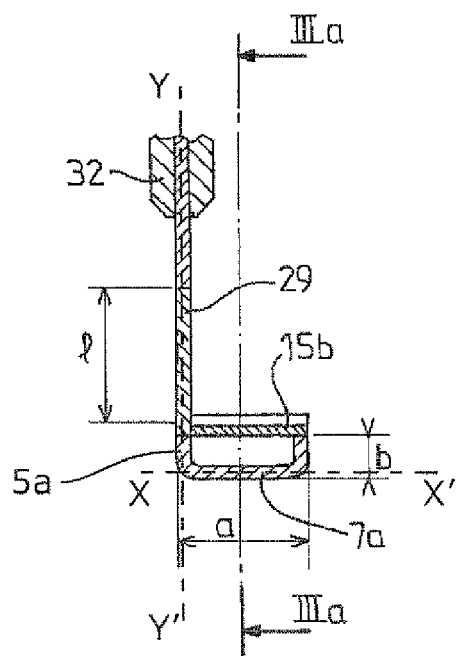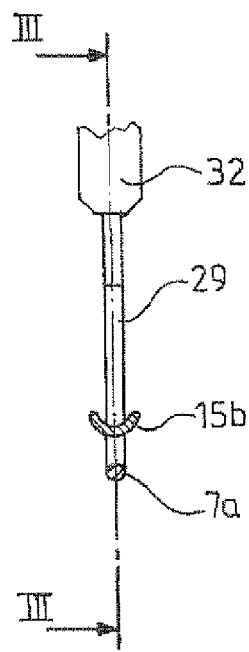
FIG. 3  FIG. 3a
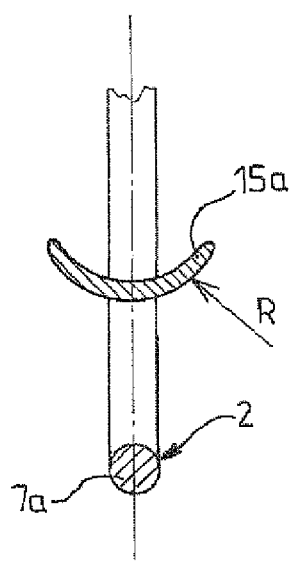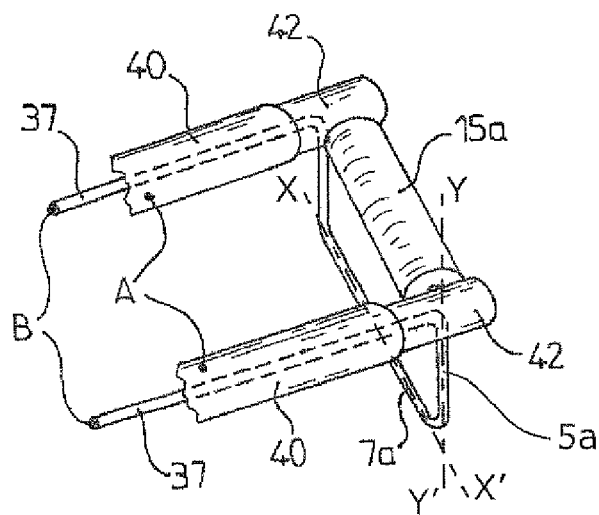
FIG. 3b  FIG. 5

CUTTING TOOL FOR TISSUE SURGICAL RESECTION

This application is a 371 of PCT/FR01/01886 Jun. 15/2001 and claims priority from France 00/07643 Jun. 15/2000.

BACKGROUND OF THE INVENTION

The present invention relates to a cutting tool intended for the surgical resection of tissues and more principally to a de-epidermization.

It is known that such a surgical act, which is effected most of the time by plastic surgeons, consists in removing the superficial layer of the skin, taking care to respect the subjacent vascularization following its course in the dermis. This surgical act, which is particularly delicate to carry out, is effected by using various blunt instruments of scissors or scalpel type. This technique is delicate, particularly by reason of the difficulty that there is to ensure a removal of the dermis which is regular in thickness.

The instruments used in the prior state of the art are not able to ensure such a regularity of the removed dermis.

SUMMARY OF THE INVENTION

It is an object of the present invention to overcome these drawbacks by proposing a cutting tool for bistoury which, without requiring particular skill, ensures, virtually automatically, a removal of a superficial layer of tissue which is regular in thickness.

The present invention thus has for its object a cutting tool intended for tissue surgical resection instruments, such as in particular electric or ultrasonic bistouries, of the type comprising a connector element which is supported in its upstream portion by the bistoury, a thin cutting element integral with the connector element, and forming a plane, and a guide element spaced apart from the cutting element by a distance equal to the thickness of the tissue elements to be removed and which is designed, during the cutting procedure, to be urged in contact with the surface thereof, characterized in that the guide element is located in the cutting element plane, and its surface adapted to be urged in contact with the tissues is larger than the corresponding surface of the cutting element.

The guide element and the cutting element will preferably have cross-sections which are at least partly circular and the radius of curvature of the guide element will be greater than that of the cutting element.

Furthermore, the guide element may be a cylindrical element whose axis will be parallel to that of the cutting element.

The guide element may be constituted by one or more rotary elements adapted to roll on the tissues to be removed when they are displaced on these latter. Such rotary elements may present a certain noteworthy coefficient of friction with respect to the tissue to be removed, which, as has been observed, improves regularity of the displacement of the cutting element.

The guide element will preferably be constituted by a cylindrical element whose axis will be parallel to that of the cutting element.

In one form of embodiment of the invention, which is simple and inexpensive to implement, the blade will be constituted by a metal wire bent to as to form a loop of substantially rectangular shape of which one of the sides will constitute the cutting element and the opposite side will constitute the guide element. This latter element may be coated with an insulating material.

In another form of embodiment of the invention, the cutting tool will comprise means for adjusting the distance existing between the cutting element and the guide element, which will enable the surgeon to effect, with the aid of the same tool, removals of different thicknesses.

This cutting tool is intended in particular to equip an electric bistoury but it may also be used on other types of bistouries such as in particular ultrasonic bistouries.

When the bistoury is an electric bistoury, the cutting element will be in electrical connection with the bistoury and the guide element will not be in electrical connection therewith. In that case, the guide element may either be made of an insulating material or be made of a conducting material provided with insulating means.

It is known that de-epidermization may be effected for different purposes and in particular for purposes of aesthetic and reconstructive surgery. It is also carried out in order to avoid the formation of epidermic cysts in the event of turning-in of a musculo-cutaneous flap, in the case of a mammary reconstruction particularly when the flap is turned in under the cutaneous envelope of the breast after ablation of the glandular tissues. Moreover, in this same domain, it is known that, when an internal mammary prosthesis is fitted, one of the complications which sometimes arises is the formation of a peri-prosthetic fibrous shell which, in the course of time, brings about a loss of suppleness of the breast as well as a deformation thereof. The treatment usually carried out consists in an exeresis of this shell by repeating the incision through which the prosthesis was fitted and which, for aesthetic reasons, is the smallest possible.

The present invention is more particularly interesting in this domain of surgery, since it makes it possible to ensure the exeresis of such a shell in particularly easy, regular and efficient manner.

Furthermore, the present invention is particularly well adapted to effecting resections under endoscopic control (hysteroscopy, cystoscopy) of the internal part of a hollow organ and in particular of the uterus, bladder or digestive tube, insofar as it allows the surgeon to be sure of not hollowing out to too great a depth.

The cutting tool according to the invention may be used with unipolar electric bistouries, but also with bipolar electric bistouries. To that end, the tool may comprise connection means making it possible to connect, on the one hand, the cutting element to one current supply pole and, on the other hand, conducting elements close to the cutting element to the other supply pole.

BRIEF DESCRIPTION OF THE DRAWINGS

Various forms of embodiment of the present invention will be described hereinafter by way of non-limiting examples, with reference to the accompanying drawings, in which:

FIG. 1 is a view in section of a cutting tool for electric bistoury according to the invention, which is disposed perpendicularly to the plane of a skin surface which it is desired to de-epidermize.

FIG. 1a is a view in transverse section of the cutting tool shown in FIG. 1 along line Ia-Ia thereof.

FIG. 2 is a partial longitudinal sectional view along a plane perpendicular to a skin surface to be de-epidermized, of a variant embodiment of the invention in which the thickness of the tissues to be removed is adjustable.

FIG. 3 is a view on a smaller scale of a cutting tool for bistoury according to the invention, of non-adjustable type.

FIG. 3a is a view in section of the tool shown in FIG. 3 along line IIIa-IIIa thereof.

FIG. 3b is an enlarged partial sectional view of the tool shown in FIG. 3a.

FIG. 4 is a view in perspective of a variant embodiment of a cutting tool according to the invention.

FIG. 4a is a schematic view in section of another example of application of the cutting tool for electric bistoury according to the invention shown in FIG. 4.

FIG. 5 is a partial view in perspective of a cutting tool according to the invention intended for use on a bipolar bistoury.

DESCRIPTION OF THE PREFERRED EMBODIMENTS

FIGS. 1 and 1a show views in section, along a plane perpendicular to a skin surface 1, of a cutting tool 3 which is intended to be connected to an electric bistoury (not shown in the drawing). This cutting tool 3 thus comprises a rod 5 of stainless steel wire which is bent in its lower part so as to form a perpendicular arm 7. This arm 7 has a length a which corresponds to the working width of the tool 3. The arm 7 terminates in a 90° bend extending in a second arm 9 parallel to the rod 5 and itself terminating in another right-angled bend so as to form an arm 11 parallel to the arm 7 and of the same length a as the latter. The end of the arm 11 comes into contact with the rod 5 and is fixed thereon, for example by means of welding spots 13. A guide element 15, constituted by an insulating and rigid cylinder, is threaded on the arm 11 and is mounted to rotate thereon. This guide element 15 defines between its periphery and the upper face of the arm 7 a space of distance b which corresponds, as explained hereinafter, to the thickness of the tissue which it is desired to remove.

The end of the rod 5 is connected to means, not shown in the drawing, for fixation of an electric bistoury of unipolar type.

Under these conditions, the bistouri according to the invention operates as indicated hereinafter. The means for supplying current to the electric bistoury being connected, the surgeon brings the arm 7 into contact with the patient's skin and drives his cutting tool until the guide element 15 comes into contact with the upper surface 1 of the skin. It then remains for the surgeon to displace the bistoury in the direction V so as to create, during this displacement, a cut-out 17 in the tissues, thus forming a flap of epidermis 19 of regular thickness b.

In an interesting form of embodiment of the invention, the distance b is adjustable, which makes it possible for the surgeon to use the same cutting tool for various interventions.

FIG. 2 shows for example such a form of embodiment. The cutting tool 3 is thus constituted by a rod 20 which is connected to the bistoury by means not shown in the drawing, and which comprises a threaded zone 22 on which is screwed an adjusting wheel 24. This wheel comprises an inner chamber in which is disposed a bush 25 which is threaded on the rod 20 and which comprises in its upper part a flange 26 which has the effect of connecting it in translation with the wheel 24 while leaving it free to rotate with respect thereto. The lower part of the rod 20 extends downwardly by a portion of arm 5a which is made of stainless steel wire and which is bent at 90° in order to form a part 7a intended to constitute the cutting element of the tool. A guide element 15a is constituted by a rigid cylinder of plastics material which is mounted for rotation about two end bosses 27 which are mounted for rotation in two corresponding recesses provided in the bush 25.

For reasons of simplification, only the left-hand half of the cutting tool 3 has been shown in FIG. 2, the other, right-hand half being identical thereto.

In order to adjust the thickness b of the tissue to be removed, it will suffice for the practitioner to screw or unscrew the wheel 24 on the threaded part 22 of the rod 20, which will have the effect of displacing it in the longitudinal direction of this rod and consequently of moving the guide element 15a towards or away from the cutting element 7a of the tool 3 depending on the direction of rotation of the wheel 24.

The outer surface of the guide element will advantageously present slight roughness, intended to create a sufficient adherence between its outer surface and the surface 1 of the skin, so that, during the displacement V, the guide element does not slide on the surface of the skin but rolls thereon. In fact, it has been observed that, by thus improving the adherence of the guide element on the surface of the skin, the regularity of the displacement of the cutting element was improved at the same time. The roughness of the outer surface of the guide element may be produced by any means, whether it be by sand-blasting or by granulometry made at moulding, etc.

In a simplified form of embodiment of the invention shown in FIG. 3, the cutting element is constituted by a stainless steel wire 29 which is supported by a bistoury head 32 and which is wound so as to form a loop. In this form of embodiment of the invention, the thickness b of the flap of removed tissue is fixed. To that end, the opposite sides 5a of the loop and the side 7a form the cutting element. The side 15b opposite to side 7a constitutes the guide element and is consequently coated with an insulating material. This same insulating material is also deposited over a length 1 of the wire 29.

The cross-section of the guide element 15b is moon-shaped, the concavity being oriented upwardly and the radius R of its base being much greater than the radius r of the cutting element. Under these conditions, the outer surface of this guide element capable of coming into contact with the tissues 1 is much larger than that of the cutting element 7a, which has the effect of promoting its guiding and smooth displacement over the tissues 1.

This form of embodiment is particularly interesting due to its low cost price which will allow the practitioner to have available a set of cutting tools of various width a and thickness b appropriate for the different interventions that he wishes to carry out.

Of course, in certain forms of embodiment of the invention, the support rod or rods 5 or 29 do not necessarily lie in the plane formed by the cutting element and the guide element, and may form any angle with said plane. In particular, they may be perpendicular thereto as shown in FIGS. 4 and 4a.

Thus, by way of example, when it is desired to effect a resection of a peri-prosthetic fibrous shell 36 which may be formed in the course of time when an internal mammary prosthesis is fitted, and which brings about a loss of suppleness of the breast as well as a deformation thereof, an angle of 90° is made between said plane and the rod 29. This allows the cutting element of the bistouri to be introduced through an incision 38 of small dimensions and to eliminate this shell 36 by a displacement substantially in the direction V' of the cutting tool 3. Such a cutting tool may also be used in combination with an electric bistoury operating in bipolar mode.

FIG. 5 thus shows a cutting tool 3 comprising two metallic support arms 40 which terminate in two insulating studs 42 made of ceramics, at the base of which is fixed a U-shaped metallic cutting element 7a. Between the two studs 42 is disposed a guide element 15a constituted by an insulating cylinder mounted for rotation about its longitudinal axis. In this form of embodiment, one of the poles A for electrical energy supply is connected to the arms 40 and the other pole B is connected to the cutting element 7a, by two insulated conductors 37 which pass through the arms 40 and which are connected to each of the ends of the cutting element 7a.

Such a cutting tool may be used in particular for various applications and in particular for effecting endoscopic resections in a saline medium.

The invention claimed is:

1. Cutting tool intended for tissue surgical resection instruments, comprising:
   a connector element (5, 5a, 29) which is supported in its upstream portion by a bistoury (32),
   a thin cutting element (7, 7a) supported by an elongated portion (5a) of the connector element that is transverse to the cutting element, a longitudinal axis (X-X') of the cutting element and a longitudinal axis (Y-Y') of the elongated portion of the connector element together defining a cutting element plane, and
   a guide element (15, 15a, 15b) spaced apart from the cutting element (7, 7a) by a distance (b) equal to the thickness of the tissue to be removed and which is designed, during the cutting procedure, to be urged in contact with the surface (1) thereof,
   wherein a longitudinal axis of the guide element (15, 15a, 15b) is located in the cutting element plane and wherein the guide element has a surface adapted to be urged in contact with the tissue that is larger than the corresponding surface of the cutting element (7, 7a).

2. Cutting tool according to claim 1, wherein the guide element (15, 15a, 15b) and the cutting element (7, 7a) have cross-sections which are at least partly circular and the radius of curvature (R) of the guide element (15, 15a, 15b) is greater than that (r) of the cutting element (7, 7a).

3. Cutting tool according to claim 2, wherein the guide element (15, 15a 15b) is a cylindrical element whose axis is parallel to that of the cutting element (7, 7a).

4. Cutting tool according to claim 2, wherein the guide element is moon-shaped in cross-section and has a concavity facing away from the cutting element.

5. Cutting tool according to claim 1, wherein the guide element (15, 15a) comprises at least one rotary element adapted to rotate when it is displaced over the surface (1) of the tissues to be removed.

6. Cutting tool according to claim 5, wherein the outer surface of the rotary element (15, 15a) has a coefficient of friction higher than a coefficient of friction of the tissues to be removed.

7. Cutting tool according to claim 1, wherein the cutting element (7, 7a) is in electrical connection with the bistoury (32), and the guide element (15, 15a, 15b) is not in electrical connection therewith.

8. Cutting tool according to claim 7, wherein the guide element (15, 15a, 15b) comprises an insulating material.

9. Cutting tool according to claim 1, comprising a metallic wire forming a loop of substantially rectangular shape, of which one of the sides (7a) constitutes the cutting element and the opposite side (15b) constitutes the guide element.

10. Cutting tool according to claim 1, further comprising means (24, 25) for adjusting the distance (b) between the cutting element (7a) and the guide element (15a, 15b).

11. Cutting tool according to claim 1, further comprising a supply of current of bipolar type.

12. Cutting tool according to claim 11, further comprising connection means (37) for connecting the cutting element (7a) to a first current supply pole (A) and connecting conducting elements (40) close to the cutting element (7a) to a second supply pole (B).

* * * * *